(12) United States Patent
Nakamura et al.

(10) Patent No.: US 8,241,872 B2
(45) Date of Patent: Aug. 14, 2012

(54) MICROORGANISM PRODUCING CYCLIC COMPOUND

(75) Inventors: Ikuko Nakamura, Tokyo (JP); Koji Yoshikawa, Tokyo (JP); Teruhisa Masaki, Tokyo (JP); Ryuichi Kanasaki, Tokyo (JP); Neelam Shahab, Selangor Darul Ehsan (MY)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/922,675

(22) PCT Filed: Mar. 13, 2009

(86) PCT No.: PCT/JP2009/054875
§ 371 (c)(1),
(2), (4) Date: Sep. 14, 2010

(87) PCT Pub. No.: WO2009/113660
PCT Pub. Date: Sep. 17, 2009

(65) Prior Publication Data
US 2011/0020872 A1    Jan. 27, 2011

(30) Foreign Application Priority Data
Mar. 14, 2008   (JP) ................. 2008-065201

(51) Int. Cl.
*C12N 1/14* (2006.01)
*C12P 21/04* (2006.01)
*C12P 1/02* (2006.01)

(52) U.S. Cl. ........ 435/70.1; 435/41; 435/71.1; 435/171; 435/243; 435/254.1; 435/256.4

(58) Field of Classification Search ................. None
See application file for complete search history.

(56) References Cited

U.S. PATENT DOCUMENTS
5,436,219 A   7/1995  Ohra et al.
5,798,379 A   8/1998  Mizukami et al.

FOREIGN PATENT DOCUMENTS
JP     10-245385       9/1998
JP     2007-269654    10/2007
JP     2007-269954    10/2007
WO     WO 92/17496    10/1992
WO     WO 93/19600    10/1993
WO     WO 2008/020260 A2   2/2008

OTHER PUBLICATIONS

Stasinopoulos et al., "Exopolysaccharide production by *Acremonium persicinum* in stirred-tank and air-lift fermentors," Appl. Microbiol. Biotechnol., vol. 36, pp. 465-468 (1992).*
International Search Report from the Japanese Patent Office for International Application No. PCT/JP2009/054875, mailing date Apr. 7, 2009.
De Marco, Antonio et al., "Complete Assignment of Carbon Signals in a Stereospecific Peptide via Selective and Single Off-Resonance Proton Decoupling Experiments. Analysis of the Carbon-13 Nuclear Magnetic Resonance Spectrum of Alumichrome at 67.88 MHz", *Biochemistry*, 1979, American Chemical Society, pp. 3846-3854, vol. 18, No. 18.
De Marco, Antonio et al., "$^1$H-$^{15}$N Spin-Spin Couplings in Alumichrome", *Biopolymers*, vol. 17, 1978, pp. 2727-2742.
Emery, Thomas, "Role of Ferrichrome as a Ferric Ionophore in *Ustilago sphaerogena*", Biochemistry, vol. 10, No. 8, 1971, pp. 1483-1488.
International Preliminary Report on Patentability for International Application No. PCT/JP2009/054876 issued Nov. 2, 1010.
International Preliminary Report on Patentability for International Application No. PCT/JP2009/054875 issued Nov. 2, 2010.
International Search Report for International Application No. PCT/JP2009/054876, mailed Apr. 28, 2009.
Krauss, Eric M. et al., "Anomalous Exchange Kinetics of Peptide Amide Protons in Aqueous Solutions", *Int. J. Peptide Protein Res.* 17, 1981, pp. 42-47.
Llinás, Miguel et al., "A Carbon-13 Spin Lattice Relaxation Study of Alumichrome at 25.1 MHz and 90.5 MHz", *Biochimica et Biophysica Acta*, 492 (1977) pp. 1-11.
Llinás, Miguel et al., "$^{27}$Al NMR, a Quadrupolar Probe for the Entatic State and Stability of Metallochromophores. A Study of Ferrichrome Peptides at 65.1 MHz", *Journal of the American Chemical Society*, 102:7, 1980, pp. 2226-2230.
Llinás, Miguel et al., "Amide Proton Spin-Lattice Relaxation in Polypeptides-A Field Dependence Study of the Proton and Nitrogen Dipoloar Interactions in Alumichrome", *Biophys.J.*, Biophysical Society, vol. 24, 1978, pp. 849-862.
Llináas, Miguel et al., "Charge Relay at the Peptide Bond. A Proton Magnetic Resonance Study of Solvation Effects on the Amide Electron Density Distribution", *Journal of the American Chemical Society*, 97:16, 1975, pp. 4731-4737.
Llinás, Miguel et al., "Nitrogen-15 Nuclear Magnetic Resonance Spectrum of Alumichrome. Detection by a Double Resonance Fourier Transform Technique", *Journal of the American Chemical Society*, 98:24, 1976, pp. 7554-7558.
Llinás, Miguel et al., Peptide Hydrogen Bonding. Conformation Dependence of the Carbonyl Carbon-13 Nuclear Magnetic Resonance Chemical Shifts in Ferrichrome. A Study by $^{13}$C-$^{15}$N Fourier Double Resonance Spectroscopy[1a], *Journal of the American Chemical Society*, 99:21, 1977, pp. 6846-6850.

(Continued)

*Primary Examiner* — Allison Ford
*Assistant Examiner* — Paul D. Pyla
(74) *Attorney, Agent, or Firm* — Finnegan, Henderson, Farabow, Garrett & Dunner, LLP

(57) ABSTRACT

A microorganism which produces compounds useful as an antifungal agent, particularly a therapeutic agent for deep-seated mycoses, such as mycotic sinusitis, is provided. The present inventors have conducted intensive studies on naturally-occurring microorganisms as a research for antifungal compounds, and found a fungus *Acremonium persicinum* which produces cyclic compounds having a potent antifungal activity and useful as a medicament, particularly an antifungal agent, and the present invention was completed.

1 Claim, 2 Drawing Sheets

OTHER PUBLICATIONS

Llinás, Miguel et al., "The Solution Conformation of the Ferrichromes-V. The Hydrogen Exchange Kinetics of Ferrichrome Analogues; The Conformational State of the Peptides", *Journal of Biological Chemistry*, vol. 248, No. 3, 1973, pp. 924-931.

Llinás, Miguel et al., "The Solution Conformation of the Ferrichromes-IV. pH Dependence of the Individual Slow Amide Hydrogen-Deuterium Exchange in Alumichrome", *The Journal of Biological Chemistry*, vol. 248, No. 3, 1973, pp. 915-923.

Llinás, M. et al., "The Structure of Two Alanine Containing Ferrichromes: Sequence Determination by Proton Magnetic Resonance",*Biophys. Struct. Mechanism 2*, 1976, pp. 105-117.

Mori, Hiroaki et al., "FR235222, a Fungal Metabollite, is a Novel Immunosuppressant that Inhibits Mammalian Histone Deacetylase-III. Structure Determination", *The Journal of Antibiotics*, vol. 56, No. 2, 2003, pp. 181-185.

Neilands, J.B., A Crystalline Organo-iron Pigment from a Rust Fungus, *Journal of the American Chemical Society*, vol. 74, No. 19, 1952,pp. 4846-4847.

Neilands, J..B., "Hydroxamic Acids in Nature", *Science*, vol. 156, No. 3781, 1967, pp. 1443-1447.

Ohra, Junko et al., "Production of the Phytotoxic Metabolite, Ferricrocin, by the Fungus *Colletotrichum gloeosporioides*", *Biosci. Biotech. Biochem.*, 59(1), 1995, pp. 113-114.

Pitt, C.G. et al., "The Selection and Evaluation of New Chelating Agents for the Treatment of Iron Overload", *The Journal of Pharmacology and Experimental Therapeutics*, vol. 208, No. 1, 1979, pp. 12-18.

Pramanik, Avijit et al., "Albomycin is an effective antibiotic, as exemplified with *Yersinia enterocolitica* and *Streptococcus pneumoniae*", *International Journal of Medical Microbiology*, vol. 297, No. 6, 2007, pp. 459-469.

Sharman, Gary J., Structural elucidation of XR586, a paptaibol-like antibiotic from *Acremonium persicinum, Biochem J.*, vol. 320, part 3,1996, pp. 723-728.

van der Helm, Dick et al., "Crystal Structure of Ferrichrome and a Comparison with the Structure of Ferrichrome A", *Journal of the American Chemical Society*, 102:12, 1980, pp. 4224-4231.

Wookey, P. et al., Involvement of Inner and Outer Membrane Components in the Transport of Iron and in Colicin B Action in *Escherichia coli*, Journal of Bacteriology, vol. 133, No. 2, 1978, pp. 661-666.

Zou, Guozhang et al., "Synthesis and properties of different metal complexes of the siderophore desferriferricrocin", *BioMetals*, vol. 18, 2005, pp. 63-74.

Lamb, Bernard C. et al., "Inherited and Environmentally Induced Differences in Mutation Frequencies Between Wild Strains of *Sordaria fimicola* From Evolution Canyon", *Genetics*, The Genetics Society of America, 149, May 1998, pp. 87-99.

Molnár, I. et al., "The biosynthetic gene cluster for the microtubule-stabilizing agents epothilones A and B from *Sorangium cellulosum* So ce90", *Chemistry & Biology*, 7, Published Jan. 5, 2000, Research Paper, pp. 97-109.

Thefreedictionary by Farlex, Google search, definition of "Strain" visited at http://www.thefreedictionary.com/strain, last viewed on Mar. 15, 2012.

Extended European Search Report for European Patent Application No. EP 09720686.6 dated Mar. 22, 2012.

Sarookhani, Mohammad Reza et al., "Isolation of *Acremonium* species producing cephalosporine C (CPC) from forest soil in Gilan province, Iran", *African Journal of Biotechnology*, Vo. 6(22), pp. 2506-2510, Nov. 19, 2007.

* cited by examiner

MICROORGANISM PRODUCING CYCLIC COMPOUND

TECHNICAL FIELD

The present invention relates to a fungus *Acremonium persicinum* which produces cyclic compounds useful as an active ingredient of a pharmaceutical composition, such as a pharmaceutical composition for the treatment of mycoses, particularly deep-seated mycoses.

BACKGROUND ART

When an antibiotic has been administered during an extended period of time, pathogenic bacteria to be targeted has been removed, but fungi resistant to antibiotics have increased. It is considered that such a situation causes deep-seated mycoses (The phenomenon in which remaining fungi remarkably increase is designated as so-called microbial substitution). Alternatively, an elderly patient, a postoperative patient, or a patient to whom an antitumor drug or an immunosuppressant is administered is subject to fungal infection, due to the suppressed biophylaxis. It is considered that fungi increased in such a patient cause deep-seated mycoses.

Therapeutic agents for deep-seated mycoses include antifungal drugs, for example, 1) a nucleic acid base drug flucytosine, based on the inhibition of DNA synthesis in fungi, and 2) a polyene macrolide amphotericin B, an imidazole derivative miconazole, and a triazole derivative fluconazole, based on the inhibition of synthesis of cell membrane in fungi.

Ferrichrome, a cyclic hexapeptide containing three ornithines, having the following chemical structure is a known compound (non-patent literature 1), but this reference does not disclose that ferrichrome has an antifungal activity.

[Chem. 1]

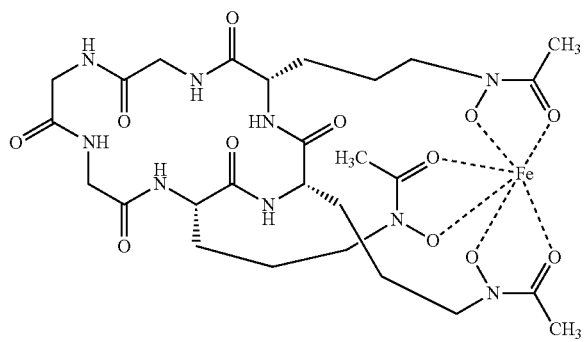

[non-patent literature 1] Journal of American Chemical Society, 1980, vol. 102, pp. 4224-4231

DISCLOSURE OF THE INVENTION

Problems to be Solved by the Invention

An object of the present invention is to provide a microorganism which produces a compound useful as an active ingredient of a pharmaceutical composition, such as a pharmaceutical composition for the treatment of mycoses, particularly deep-seated mycoses.

Means for Solving the Problems

The present inventors have conducted intensive studies on naturally-occurring microorganisms as a research for antifungal compounds, and found that a fungus *Acremonium persicinum* strain designated as MF-347833 produces compounds having a potent antifungal activity. Further, the present inventors focused on the culture broth of the strain, and accomplished the isolation of cyclic compounds having a potent antifungal activity from the culture broth, and thus the present invention was completed.

The present invention relates to a fungus *Acremonium persicinum* which produces a compound of the formula (I) or a salt thereof.

[Chem. 2]

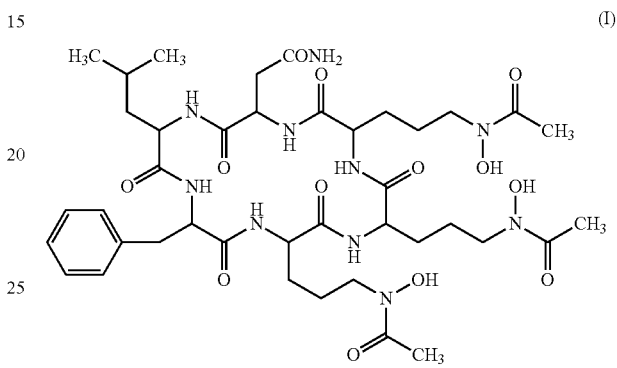

Effects of the Invention

The fungus *Acremonium persicinum* can produce a compound of the formula (I) or a salt thereof, which may be used as an agent for preventing and/or treating mycoses, particularly deep-seated mycoses or the like.

BRIEF DESCRIPTION OF THE DRAWINGS

FIG. 1 is a chart showing the $^1$H-NMR spectrum of compound A (Solvent for measurement: $d_6$-DMSO).
FIG. 2 is a chart showing the $^{13}$C-NMR spectrum of compound A (Solvent for measurement: $d_6$-DMSO).
FIG. 3 is a chart showing the $^1$H-NMR spectrum of compound B (Solvent for measurement: $d_6$-DMSO).
FIG. 4 is a chart showing the $^{13}$C-NMR spectrum of compound B (Solvent for measurement: $d_6$-DMSO).

BEST MODE FOR CARRYING OUT THE INVENTION

Figure 1:
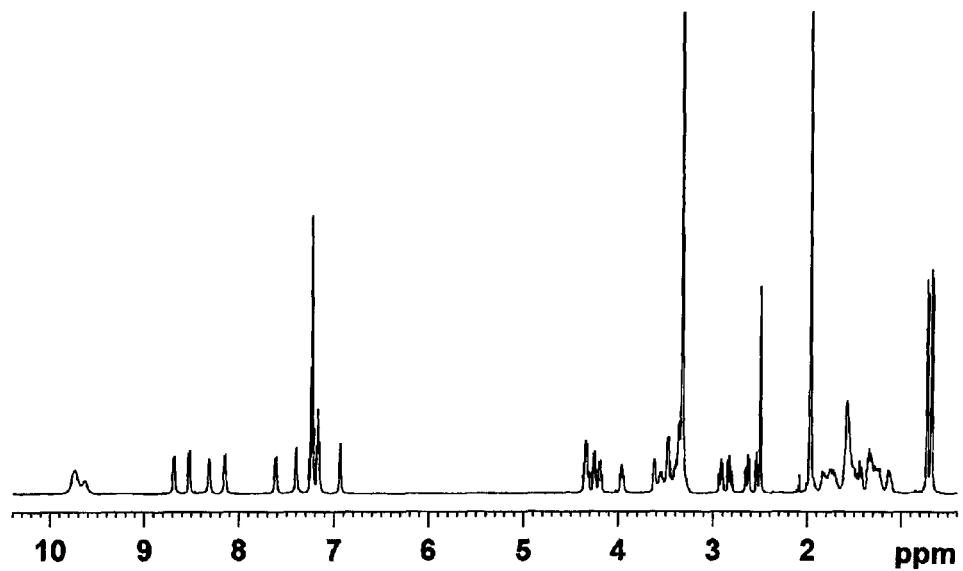
[FIG. 1]

The present invention will be explained in detail hereinafter.

Mycological characteristics of a microorganism which produces the compound of the formula (I) or a salt thereof will be described below.

(1) Origin of Producing Strain

The fungus strain MF-347833 of genus *Acremonium* was isolated from leaf litter collected in the Endau Rompin national park, Johore, Malaysia. This strain has been deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) as FERM BP-10916 (deposit date: Oct. 10, 2007).

(2) Morphological Characteristics of Producing Strain

The morphological characteristics of the strain was determined on the basis of the observations of its form on a potato dextrose agar medium. The growth of the strain on a potato dextrose agar medium (Difco 2010) was rapid. Colonies grew to a diameter of 39-41 mm at 25° C. in 2 weeks, and conidia were formed. The surfaces of the colonies were floccose, and the margins thereof were undulate. Each colony was radiately sulcate from the center to the margin, but it was difficult to identify these sulcate striates from the surface. The colonies were white (1A1), but yellowish white (4A2) at the center thereof. The sulcates which radiated from the center to the margin could be identified from the reverse. The colonies were generally ivory (4A3), but mustard brown (5E6) at the center. Colonies attained approximately 24 mm in diameter at 30° C. two weeks later, and no growth was observed at 5° C. and at 37° C.

The strain grew rapidly on a corn meal agar medium (Difco 0386), and the colonies spread to a diameter of 39-40 mm at 25° C. in 2 weeks. The surface of each colony was felty. The margin thereof was undulate, and the colonies were not sulcate. The surface was white (1A1), and the reverse was also white (1A1). Colonies attained a diameter of 14 mm at 30° C. in 2 weeks, and were not sulcate. No growth was observed at 5° C. and at 37° C.

Vegetative hyphae were 1.8-2.7 μm in width, and chlamydospore absent. Conidiophores were hyaline, not branched, and arised singly from a single vegetative hypha or plectonematogenous hyphae. Many warts on conidiophore and the base thereof was septate. Conidial ontogeny was phialidic, and the length from the base of each conidiophore to the apex of phialides was 33-40 μm. Conidia were hyaline, ellipsoidal, 3.7 to 4.5×2.8 to 3.2 μm (average: 4×3 μm) in size, aggregated in mass at the apex of phialides, but never in chain. The surface of conidia appeared smooth by the observation with an optical microscope (×400), but a roughly concavo-convex pattern could be observed with an electron microscope (×9000).

The morphological characteristics indicate a possibility that the strain belongs to the genus *Acremonium*. A comparison was made on the basis of Cephalosporium-artige Schimmelpilze (Hyphomycetes)/Walter Gams (1971), and as a result, the morphological characteristics of the strain accorded with those of *Acremonium persicinum* in the section Gliomastix. Further, as a result of a homology search with respect to a 28S rDNA and an 18S rDNA of the strain, these rDNAs were included in the clade of *Acremonium persicinum* in the section Gliomastix. The conclusion from the morphological characteristics was consistent with that from the genetic characteristics. The strain was identified as *Acremonium persicinum*, and designated as *Acremonium persicinum* strain MF-347833.

(3) Cultural Characteristics

The cultural characteristics of the strain were determined on commercially available media and media prepared in accordance with compositions described in a reference. As a potato dextrose agar medium, a Sabouraud dextrose agar medium, an Emerson YpSs agar medium, a corn meal agar medium, and an oatmeal agar medium, Difco 2010, Difco 0109, Difco 0739, Difco 0386, and Difco 0552 were purchased, respectively. A malt extract agar medium, a Czapek solution agar medium, and an MY20 agar medium were prepared in accordance with the compositions described in a JCM catalog (Nakase, T. 6th ed., pp. 617, Japan Collection of Microorganisms, the Institute of Physical and Chemical Research, Saitama, 1995).

TABLE 1

Cultural characteristics of *Acremonium persicinum* strain MF-347833

| Media | Cultural characteristics |
|---|---|
| Malt extract agar | Growth: Rapidly. 30-31 mm in diameter. Surface: Circular, undulate at margin, floccose, white (1A1). Reverse: Pale yellow to pale orange (5A3). |
| Potato dextrose agar (Difco 2010) | Growth: Rapidly. 39-41 mm in diameter. Surface: Circular, undulate at margin, floccose, white (1A1) to yellowish white (4A2). Reverse: Sulcate, ivory (4A3). Mustard brown at center (5E6). |
| Czapek solution agar | Growth: Rapidly. 57-59 mm in diameter. Surface: Circular, entire at margin. Felty, somewhat reddish gray at center, generally white (1A1). Reverse: Pale orange (5A2). |
| Sabouraud dextrose agar (Difco 0109) | Growth: Rapidly. 32-33 mm in diameter. Surface: Circular, undulate at margin. Forming striates. Floccose, white (1A1). Reverse: Sulcate, yellowish white (4A2). |
| Emerson YpSs agar (Difco 0739) | Growth: Rapidly. 36-38 mm in diameter. Surface: Circular, undulate at margin. Felty, generally white (1A1). Reverse: Pale orange (5A2). |
| Corn meal agar (Difco 0386) | Growth: Rapidly. 39-40 mm in diameter. Surface: Circular, undulate at margin. Felty, generally white (1A1). Reverse: White (1A1). |
| MY20 agar | Growth: Rapidly. 34-35 mm in diameter. Surface: Circular, entire at the margin. Floccose, generally white (1A1). Reverse: Pale yellow (4A4). |
| Oatmeal agar (Difco 0552) | Growth:Rapidly. 50-51 mm in diameter. Surface: Circular, entire at the margin. Floccose, yellowish white (4A2) at center, generally white (1A1). Reverse: Pale yellow (4A4). |

The fungus strain MF-347833 was inoculated onto each agar medium, and observed after cultivation at 25° C. for 14 days. Colors were determined in accordance with Methuen Handbook of Colour (Kornerup, A. and J. H. Wanscher, 3rd ed., pp. 252, Methuen, London, 1987). Growth temperatures were determined on the potato dextrose agar medium (Difco 2010).

The strain sometimes shows artificial or naturally-occurring variations. The fungus *Acremonium persicinum* strain MF-347833 used in the present invention includes not only the originally isolated strain, but also artificial variations caused by ultraviolet rays, radiation rays, chemical agents, or the like, and naturally-occurring variations.

The compound of the formula (I) sometimes forms a salt with a base. As such a salt, there may be mentioned, for example, salts with an inorganic base, such as sodium, potassium, magnesium, calcium, or the like, or salts with organic base, such as methylamine, ethylamine, ethanolamine, lysine, ornithine, or the like. The salts as used herein include so-called a complex salt and a chelate compound. A metal which forms such a salt may be a divalent or trivalent metal, such as iron, aluminum, or the like.

Hereinafter, a free form of the compound of the formula (I), an aluminum salt of the compound of the formula (I) and an iron salt of the compound of the formula (I) are sometimes referred to as compound A, compound B, and compound C, respectively.

The compound of the formula (I) exists as several geometric isomers. The compound of the formula (I) is sometimes shown only as a single isomer in this specification, but the present invention includes isomers other than the single isomer, and further includes isolated isomers and mixtures thereof.

The compound of the formula (I) sometimes one or more asymmetric carbon atoms, and there may be several optical isomers, based on the asymmetric carbon atoms. The present invention includes isolated optical isomers and mixtures thereof.

The present invention includes various hydrates, solvates, and crystal forms of the compound of the formula (I) or a salt thereof, and further includes various compounds labeled with a radioisotope or a nonradioisotope.

(Process of Production)

The compound of the formula (I) or a salt thereof may be obtained by culturing the microorganism of the present invention in accordance with general cultivation methods of microorganisms.

The medium to be used is not particularly limited, so long as it contains nutrient sources capable of being utilized by the fungus *Acremonium persicinum* strain MF-347833. A synthetic medium, a semisynthetic medium, or a natural medium may be used. With regard to the medium composition, L-arabinose, D-xylose, D-glucose, D-fructose, sucrose, inositol, L-rhamnose, raffinose, D-mannitol, mannose, melibiose, lactose, D-galactose, maltose, trehalose, salicin, xanthine, chitin, starch, glucose, dextrin, glycerol, vegetable oil, or the like may be used as the carbon source. As the nitrogen source, meat extract, peptone, gluten meal, cottonseed meal, soybean powder, peanut powder, fish meal, corn steep liquor, dry yeast, yeast extract, ammonium chloride, ammonium sulfate, ammonium nitrate, uric acid, or other organic or inorganic nitrogen sources may be used. If desired, sulfate, nitrate, carbonate, phosphate, or the like of sodium, potassium, magnesium, calcium, zinc, iron, cobalt, or the like may added as metal salts. Further, a compound for promoting generation or an antifoaming agent, such as methionine, cysteine, cystine, thiosulfate, methyl oleate, lard oil, silicon oil, surfactants, or the like, may be added, if desired.

With respect to the culturing condition, it is generally preferred to culture the strain under aerobic conditions, at the temperature of 8.9 to 31.2° C., preferably approximately 26.0 to 27.6° C. The culturing period may be appropriately selected in accordance with the composition of the medium or conditions of temperature, but is generally about 1 to 30 days, preferably about 2 to 7 days.

The compound of the formula (I) or the salt thereof may be purified and isolated from a culture in accordance with conventional methods of purifying and isolating a physiologically active substance from a culture of a common microorganism. More particularly, a culture is extracted with an appropriate organic solvent, and a desired substance is purified and isolated from the resulting extract. That is, the separation and purification is carried out, using an antifungal activity as an index, by methods which utilize the difference in solubility to an appropriate solvent, or the like, and are used in preparing a common physiologically active substance. These methods may be appropriately used, alone, in a desired combination thereof, or repeatedly. As other methods for purification, a culture per se, or a supernatant prepared by removing the fungus from a culture by centrifugation or filtration, may be subjected to methods which utilize the difference in solubility to an appropriate solvent, the difference in the rate of precipitation from a solution, the difference in adsorptive affinity to various adsorbents, the difference in distribution between two liquid phases, or the like. For example, a culture liquid may be brought into contact with an appropriate carrier, and an adsorbed compound may be eluted with an appropriate solvent from the carrier to purify the compound. These methods may be appropriately used, alone, in a desired combination thereof, or repeatedly.

The compound of the formula (I) or a salt thereof may be obtained by culturing the microorganism of the present invention in a nutrient medium, and separating the compound from the resulting culture in accordance with a conventional method. The microorganism used in the production of the compound of the formula (I) or a salt thereof is not particularly limited, so long as it belongs to the genus *Acremonium* capable of producing the compound of the formula (I) or a salt thereof.

The pharmaceutical composition comprising one, or two or more of the compound of the formula (I) or salts thereof as the active ingredient may be prepared in accordance with commonly-used methods, using excipients generally used in the field, such as pharmaceutical excipients, pharmaceutical carriers, or the like.

Examples of administration include oral administration by tablets, pills, capsules, granules, powders, liquids, and the like, and parenteral administration by injections (e.g., intraarticular, intravenous, intramuscular, or the like), suppositories, ophthalmic solutions, ophthalmic ointments, transdermal liquids, ointments, transdermal attachments, transmucosal liquids, transmucosal plasters, inhalation agents, and the like.

For a solid formulation for oral administration, tablets, powders, granules, or the like may be used. Such a solid formulation may be prepared by mixing one, or two or more of the active ingredients with at least one inert excipient, such as lactose, mannitol, glucose, hydroxypropyl cellulose, microcrystalline cellulose, starch, polyvinylpyrrolidone, magnesium aluminate metasilicate, and/or the like. The composition may contain inert additives, for example, lubricants such as magnesium stearate, disintegrators such as sodium carboxymethyl starch or the like, stabilizers, or auxiliary dissolution agents, in accordance to conventional methods. The tablets or pills may be coated with a sugar coating or a film of a gastric or enteric substance, if desired.

The liquid composition for oral administration includes pharmaceutically acceptable emulsions, solutions, suspensions, syrups, elixirs, or the like, and contains commonly-used inert solvents, such as distilled water or ethanol. In addition to the inert solvents, the liquid composition may contain auxiliary agents (such as solubilizers, moistening agents, or suspending agents), sweeteners, flavors, aromatic agents, or preservatives.

The injections for parenteral administration include sterile, aqueous or non-aqueous liquids, suspensions, and emulsions. The aqueous solvent includes, for example, distilled water for injections and physiological saline. The non-aqueous solvent includes, for example, propylene glycol, polyethylene glycol, vegetable oils such as olive oil, alcohols such as ethanol, polysorbate 80 (name in Pharmacopeia), and the like. Such compositions may further contain isotonic agents, preservatives, moistening agents, emulsifying agents, dispersants, stabilizers, or auxiliary dissolution agents. These compositions may be sterilized, for example, by filtration through a bacteria retaining filter, blending of a germicide, or irradiation. Alternatively, they may be used by first making them into sterile solid compositions and dissolving or suspending them in sterile water or other sterile solvent for injection use prior to their use.

External preparations include ointments, plasters, creams, jellies, poultices, sprays, lotions, ophthalmic solutions, ophthalmic ointments, and the like. Such preparations contain commonly-used ointment bases, lotion bases, aqueous or nonaqueous liquids, suspensions, emulsions, or the like. The examples of the ointment or lotion bases are polyethylene glycol, propylene glycol, white petrolatum, white beeswax, polyoxyethylene hydrogenated castor oil, glyceryl monostearate, stearyl alcohol, cetyl alcohol, lauromacrogol, sorbitan sesquioleate, and the like.

Transmucosal agents such as inhalation agents and transnasal agents may be used in solid, liquid, or semi-solid forms, and may be prepared by conventional methods. For example, known excipients, pH adjusters, preservatives, surfactants, lubricants, stabilizers, thickeners, or the like may be added, if desired. For the administration, appropriate devices for inhalation or insufflation may be used. For example, using known devices (such as an inhalation device for measured administration) or sprayers, the compound may be administrated alone, or may be administered in a powder form of a formulated mixture or as a solution or suspension with a pharmaceutically acceptable carrier. An inhalation device for dry powder or the like may be a device for single administration or plural administrations, and a dry powder or a powder-containing capsule may be used. Alternatively, the compound may be administered in the form of an aerosol spray under pressure, or the like, using an appropriate agent for ejection, for example, an appropriate gas such as chlorofluoroalkane, hydrofluoroalkane, carbon dioxide, or the like.

In the case of oral administration, the usual dosage is about 0.01 to 100 mg/kg, preferably 0.1 to 10 mg/kg per day, which is administered in one portion or two to four portions. In the case of intravenous administration, the usual dosage is about 0.01 to 100 mg/kg per day, which is administered once or several times a day. The dose is approximately determined by taking into consideration each case, for example, symptoms, age, sex, or the like of each patient to be administered.

The compound of the formula (I) or a salt thereof may be used together with various agents of treating or preventing diseases for which the compound of the formula (I) or a salt thereof is considered to be effective. The administration may be carried out simultaneously, or successively without interval or with an appropriate interval. The simultaneous administration may be performed in the form of a single formulation, or in the form of discrete formulations.

EXAMPLES

The process for preparing the compound of the formula (I) or a salt thereof will be further illustrated by the following Examples, but the present invention is not limited to the compounds described below. Further, the process for preparing the compound of the formula (I) or a salt thereof is not limited to the specific processes described in the following working examples, and the compound of the formula (I) or a salt thereof may be prepared by the combination of these processes, or a conventional method obvious to the skilled in the art.

The abbreviations shown in Table 2 will be used in the following Examples, Preparative Examples, and Tables.

TABLE 2

| Abbreviations | Full names |
| --- | --- |
| $AlK(SO_4)_2 \cdot 12H_2O$ | Aluminum potassium sulfate dodecahydrate |
| $CHCl_3$ | Chloroform |
| $FeCl_3 \cdot 6H_2O$ | Iron (III) chloride hexahydrate |
| KCl | Potassium chloride |
| $KH_2PO_4$ | Potassium dihydrogenphosphate |
| MeCN | Acetonitrile |
| MeOH | Methanol |
| $MgSO_4 \cdot 7H_2O$ | Magnesium sulfate heptahydrate |
| $NaNO_3$ | Sodium nitrate |
| $(NH_4)_2SO_4$ | Ammonium sulfate |
| TFA | Trifluoroacetic acid |
| HR ESI MS | High resolution electrospray ionization MS |

Example 1

Cultivation Production of Compound A

A seed medium 1 (see Table 3, 30 mL) was poured into an Erlenmeyer flask (size: 100 mL) and sterilized by autoclaving (121° C., 30 minutes). A loopful of the fungus strain MF-347833 was aseptically inoculated from a slant culture into the seed medium 1, and cultured at 25° C. for 4 days while shaking on a rotary shaker (220 rpm). Next, a production medium 1 (see Table 4, 100 mL) was poured into an Erlenmeyer flask (size: 500 mL) and sterilized by autoclaving (121° C., 30 minutes). The seed culture (2 mL) was aseptically inoculated into this flask, and cultured at 25° C. for 7 days while shaking on a rotary shaker (220 rpm). The cultivation was monitored by HPLC (Analytical HPLC1; With respect to the conditions, see Table 5).

TABLE 3

Seed medium 1

| Medium components | Contents (%) |
| --- | --- |
| Cornstarch | 2 |
| Glycerol | 1 |
| Sucrose | 1 |
| Pharma media | 1 |
| Gluten meal | 1 |
| Tween 80 | 0.2 |

TABLE 4

Production medium 1

| Medium components | Contents (%) |
| --- | --- |
| Glucose | 0.5 |
| Soluble starch (Nacalai Tesque) | 1.5 |
| Yeast extract (Wako Pure Chemical Industries) | 0.5 |
| KCl | 0.02 |
| $MgSO_4 \cdot 7H_2O$ | 0.02 |
| $KH_2PO_4$ | 0.1 |
| $NaNO_3$ | 0.2 |

TABLE 5

| Conditions in analytical HPLC1 | |
| --- | --- |
| Column | Mightysil RP-18 GP 150-4.6 (5 μm), Kanto Chemical |
| Mobile phase | MeCN:water = 28:72 (v/v) (containing 0.5% NH$_4$H$_2$PO$_4$) |
| Flow rate | 1 mL/min. |
| Wavelength for detection | 210 nm |
| Retention time | Approximately 4.2 min. |

(Isolation and Purification of Compound A)

To the culture (2.6 L) obtained by the above cultivation method, an equal volume of acetone was added. This mixture was stirred for 1 hour, and filtered to obtain a culture extract. The resulting culture extract liquid was mixed with a twofold volume of water, and applied to a Diaion SP 850 column (size: 400 mL; Mitsubishi Chemical). The elution was carried out using a mixed solvent [acetone:water=30:70 (v/v), 1.9 L].

The resulting eluate was mixed with water (2.1 L). The whole was applied to a Daisogel SP-120-ODS-B column (size: 350 mL, 15/30 μm; DAISO), and eluted with a mixed solvent [MeCN:water=25:75 (v/v), 340 mL].

To this eluate, water (350 mL) was added, and applied to an OASIS HLB cartridge (size: 6 g; Waters), and eluted with MeOH (150 mL). The obtained eluate was concentrated under reduced pressure, and acetone was added to the concentrate to obtain a precipitate. This precipitate was dried to obtain yellow powder (100 mg).

A portion (15 mg) of this yellow powder was dissolved in a small quantity of MeOH, and purified by preparative HPLC1 (With respect to the conditions, see Table 6). A peak at the elution time of approximately 22 minutes was collected. The collected fraction was mixed with an equal volume of water, and applied to an OASIS HLB cartridge (size: 500 mg). Water (50 mL) was passed through the cartridge, and the elution was carried out using MeOH (50 mL). This eluate was concentrated under reduced pressure, and acetone was added to the concentrate to obtain a precipitate. This precipitate was dried to obtain the compound A (13 mg) as white powder.

TABLE 6

| Conditions in preparative HPLC1 | |
| --- | --- |
| Column | Symmetry 7 μm C18 column, 19 × 300 mm, Waters |
| Mobile phase | MeCN:water = 27:73 (v/v) (containing 0.05% TFA) |
| Flow rate | 7 mL/min. |

(Physiochemical Properties of Compound A)

The compound A purified and isolated by the above process showed the physiochemical properties shown in Table 7.

TABLE 7

Figure 2:
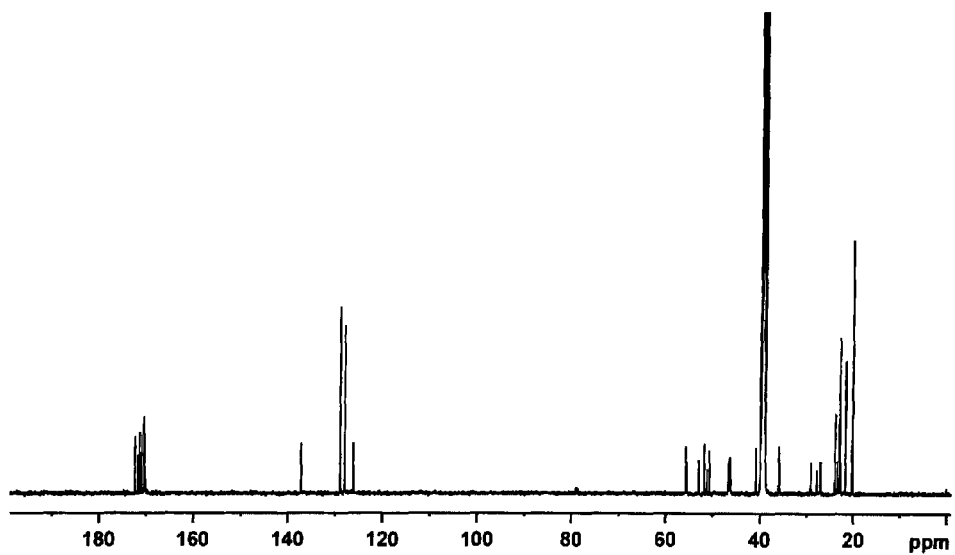
[FIG. 2]

| Physiochemical properties of compound A | |
| --- | --- |
| Color and form | White powder |
| Optical rotation | $[\alpha]_D^{25}$ − 57° (c 0.01, MeOH) |
| Molecular formula | C$_{40}$H$_{62}$N$_{10}$O$_{13}$ |
| HR ESI-MS | Found 891.4592 (M + H)$^+$, Calcd 891.4576 |
| IR (KBr) cm$^{-1}$ | 3300, 2950, 1680, 1650, 1640, 1540, 1460, 1420, 1240, 1210, 1160, 1040, 970 |
| $^1$H-NMR spectrum | Shown in FIG. 1 |
| $^{13}$C-NMR spectrum | Shown in FIG. 2 |

It was concluded from the physiochemical properties that the compound A has a chemical structure of the following formula (II). Further, the configurations of constituent amino acids were concluded to be D-Phe, L-Leu, and L-Asn in accordance with a modified Marfey's method. With respect to the ornithine portion, we compared the compound A with a naturally-occurring analogue Ferrichrome (non-patent literature 1), and presumed it to be L-ornithine, because an analysis of amino acids showed that three amino acids were identical.

[Chem. 3]

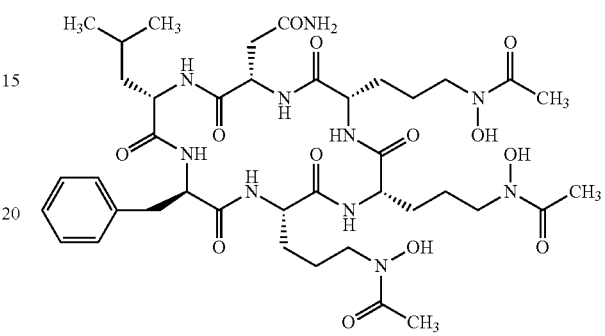

(II)

Example 2

Cultivation Production of Compounds B and C

A seed medium 2 (see Table 8, 30 mL) was poured into an Erlenmeyer flask (size: 100 mL) and sterilized by autoclaving (121° C., 30 minutes). A loopful of the fungus strain MF-347833 was aseptically inoculated from a slant culture into the seed medium, and cultured at 25° C. for 4 days while shaking on a rotary shaker (220 rpm).

The same seed medium (160 mL) was poured into an Erlenmeyer flask (size: 500 mL) and sterilized by autoclaving (121° C., 30 minutes). The seed culture (3.2 mL) was aseptically inoculated into this seed medium, and cultured at 25° C. for 3 days while shaking on a rotary shaker (220 rpm).

Next, a previously-prepared production medium 2 (see Table 9, 20 L) was poured into a jar fermentor (size: 30 L) and sterilized (121° C., 30 minutes). The seed culture (480 mL) was aseptically inoculated into the jar fermentor, and cultured at 25° C. for 7 days under aeration at 20 L/min and agitation at 200 rpm. The cultivation was monitored by HPLC (Analytical HPLC2; With respect to the conditions, see Table 11).

When a production medium 3 was used instead of the production medium 2, the above cultivation production could be carried out under the same culturing conditions.

TABLE 8

| Seed medium 2 | |
| --- | --- |
| Medium components | Contents (%) |
| Cornstarch | 2 |
| Glycerol | 1 |
| Sucrose | 1 |
| Pharma media | 1 |
| Gluten meal | 1 |
| Tween 80 | 0.2 |

TABLE 9

Production medium 2

| Medium components | Contents (%) |
|---|---|
| Glucose | 0.5 |
| Soluble starch (Nacalai Tesque) | 1.5 |
| Yeast extract (Wako Pure Chemical Industries) | 0.5 |
| Adekanol LG-109 (ADEKA) | 0.05 |
| Silicone KM-70 (Shin-Etsu Chemical) | 0.05 |
| KCl | 0.02 |
| $MgSO_4 \cdot 7H_2O$ | 0.02 |
| $KH_2PO_4$ | 0.1 |
| $NaNO_3$ | 0.2 |

TABLE 10

Production medium 3

| Medium components | Contents (%) |
|---|---|
| Sucrose | 4 |
| Dry yeast (Asahi Food and Healthcare) | 1.5 |
| $(NH_4)_2SO_4$ | 0.5 |
| Calcium carbonate | 0.5 |

TABLE 11

Conditions in preparative HPLC2

| | |
|---|---|
| Column | Mightysil RP-18 GP 150-4.6 (5 μm), Kanto Chemical |
| Mobile phase | $MeCN:H_2O$ = 28:72 (v/v) (containing 0.5% $NH_4H_2PO_4$) |
| Flow rate | 1 mL/min. |
| Wavelength for detection | 210 nm |
| Retention time | Compound B (about 8.7 min.), Compound C (about 10 min.) |

(Isolation and Purification of Compounds B and C)

To the culture (production medium 2: 90 L) obtained by the above cultivation method, an equal volume of acetone was added. This mixture was stirred for 1 hour, and filtered to obtain a culture extract. The resulting culture extract liquid was mixed with an equal volume of water, and applied to a Diaion SP 850 column (10 L; Mitsubishi Chemical). The elution was carried out using a mixed solvent [acetone:water=40:60 (v/v), 40 L].

To the resulting eluate, an equal volume of water was added. The whole was applied to a Daisogel SP-120-ODS-B column (15/30 μm, size: 2 L; DAISO), and eluted with a mixed solvent [MeCN:water=25:75 (v/v), 7 L].

To this eluate, an equal volume of water was added. The whole was applied to the Daisogel SP-120-ODS-B column (size: 2 L) again, and eluted with a mixed solvent [MeCN:water=27.5:72.5 (containing 0.05% TFA) (v/v)].

To this eluate, an equal volume of water was added. The whole was applied to the Daisogel SP-120-ODS-B column (size: 180 mL) again, and eluted with MeOH. The obtained eluate was concentrated under reduced pressure.

The resulting residue was dissolved in a small quantity of MeOH, and purified by preparative HPLC2 (With respect to the conditions, see Table 12).

A fraction at the elution time of approximately 24 to 25 minutes was mixed with an equal volume of water, and applied to an OASIS HLB cartridge (size: 6 g; Waters). Water (100 mL) was passed through the cartridge, and the elution was carried out using MeOH (100 mL). This eluate was concentrated under reduced pressure, substituted with water, and lyophilized to obtain the compound C (130 mg) as powder. This powder was crystallized using solvents (MeOH, ethyl acetate, and n-hexane) to obtain the compound C as orange crystals.

The above procedure was repeated, except that another fraction at the elution time of approximately 19 to 21 minutes was used, to obtain powder. This powder was dissolved in $CHCl_3$, and purified by a silica gel column chromatography (Spherical 60N, neutral, 40-100 μm, Kanto Chemical; $CHCl_3$:MeOH=10:1). The resulting eluate was concentrated under reduced pressure, substituted with water, and lyophilized to obtain the compound B (150 mg) as white powder. This white powder (109 mg) was crystallized using solvents (MeOH, ethyl acetate, and n-hexane) to obtain the compound B (90.1 mg) as colorless crystals.

TABLE 12

Conditions in preparative HPLC2

| | |
|---|---|
| Column | Mightysil RP-18 GP column, 250 × 20 mm ID., Kanto Chemical |
| Mobile phase | MeCN:water = 30:70 (v/v) (containing 0.05% TFA) |
| Flow rate | 10 mL/min. |

(Physiochemical Properties of Compound B)

The compound B purified and isolated by the above process showed the physiochemical properties shown in Table 13, and thus, we presumed it to be a compound in which the ratio of the compound to aluminum is 1:1.

TABLE 13

Physiochemical properties of compound B

Figure 3:
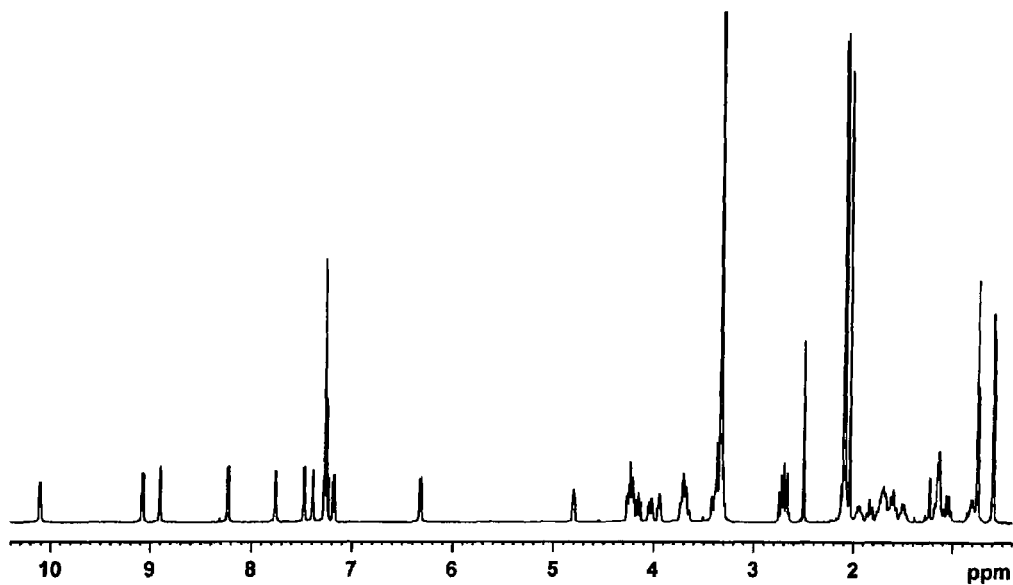
[FIG. 3]
Figure 4:
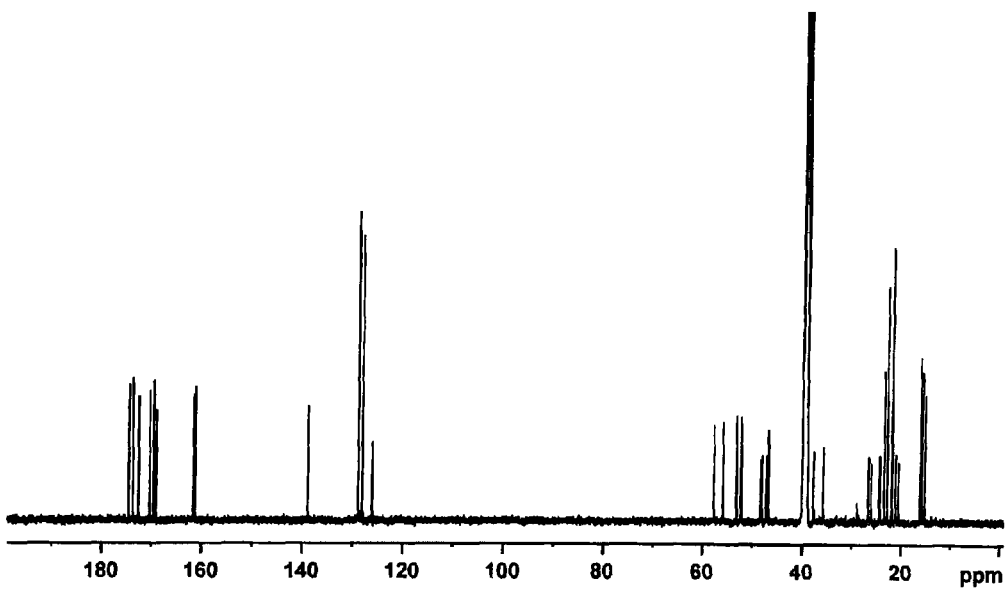
[FIG. 4]

| | |
|---|---|
| Color and form | Colorless crystals |
| Optical rotation | $[\alpha]_D^{25}$ + 210° (c 0.01, MeOH) |
| Molecular formula | $C_{40}H_{59}AlN_{10}O_{13}$ |
| HR ESI-MS | Found 915.4191 $(M + H)^+$, Calcd 915.4157 |
| IR (KBr) $cm^{-1}$ | 3300, 2930, 1680, 1650, 1620, 1520, 1370, 1240, 1140, 990 |
| Melting point | 295° C. |
| $^1H$ NMR spectrum | Shown in FIG. 3 |
| $^{13}C$ NMR spectrum | Shown in FIG. 4 |

(Physiochemical Properties of Compound C)

From single crystal X-ray structural analysis and the fact that the compound C purified and isolated by the above process showed the physiochemical properties shown in Table 14, and thus, we determined it to be a compound in which the ratio of the compound to iron is 1:1.

TABLE 14

Physiochemical properties of compound C

| | |
|---|---|
| Color and form | Orange crystals |
| Optical rotation | $[\alpha]_D^{25}$ + 256° (c 0.01, MeOH) |
| Molecular formula | $C_{40}H_{59}FeN_{10}O_{13}$ |
| HR ESI-MS | Found 944.3693 $(M + H)^+$, Calcd 944.3691 |
| Single crystal X-ray structural analysis | a = 13.850 (1) Å, b = 15.135 (1) Å, c = 24.290 (2) Å, V = 5091.6 (6) Å$^3$ |

Example 3

Assay of Antifungal Activity

Antifungal activities for test fungi shown in Table 15 was determined by a broth microdilution method (Hikaru Kume and Toshikazu Yamazaki, Clinical Microbiology, Vol. 21, No.

5, pp. 573-580, 1994). The result of the assay for antifungal activities of the compound B against the test fungi is shown in Table 15.

TABLE 15

Minimum effective concentrations (MEC) of compound B

| Test fungi | MEC (μg/mL) |
|---|---|
| Candida krusei FP1979 | 0.31 |
| Candida glabrata FP1944 | 0.31 |
| Candida guilliermondii FP2086 | 0.31 |
| Candida parapsilosis FP1980 | 0.39 |
| Cryptococcus neoformans FP1739 | 0.2 |
| Aspergillus fumigatus FP1305 | 0.31 |
| Aspergillus terreus SR0174 | 0.31 |
| Aspergillus niger ATCC6275 | 0.78 |
| Aspergillus flavus ATCC9643 | 0.2 |
| Trichosporon asahi FP2044 | 0.2 |
| Fusarium solani FP1930 | 0.2 |
| Pseudallescheria boydii FP1987 | 0.2 |
| Rhizopus oryzae FP1988 | 25 |
| Trichophyton mentagrophytes FP2103 | 0.78 |
| Trichophyton rubrum FP596 | 1.25 |
| Alternaria alternata AHU9258 | 0.1 |

As a result, it was confirmed that the compound of the formula (I) or a salt thereof has an antifungal activity. The compound of the formula (I) or a salt thereof can be used in the treatment or the like of mycoses, particularly deep-seated mycoses or the like, such as mycotic sinusitis.

As described above, it was confirmed that a fungus *Acremonium persicinum* strain MF-347833 is a microorganism which produces the compound of the formula (I) or a salt thereof which is useful and can be used in the treatment or the like of mycoses, particularly deep-seated mycoses or the like, such as mycotic sinusitis.

Industrial Applicability

The microorganism of the present invetnion, *Acremonium persicinum* strain designated as MF-347833, produces the compound of the formula (I) or a salt thereof having a potent antifungal activity. The obtained compound of the formula (I) or a salt thereof can be used as an agent for preventing and/or treating mycoses, particularly, deep-seated mycoses or the like.

Although the present invention has been described with reference to specific embodiments, various changes and modifications obvious to those skilled in the art are possible without departing from the scope of the appended claims.

The invention claimed is:

1. An isolated strain *Acremonium persicinum* MF-347833 of Deposit No. FERM BP-10916, wherein said isolated strain produces a compound of the formula (I) or a salt thereof

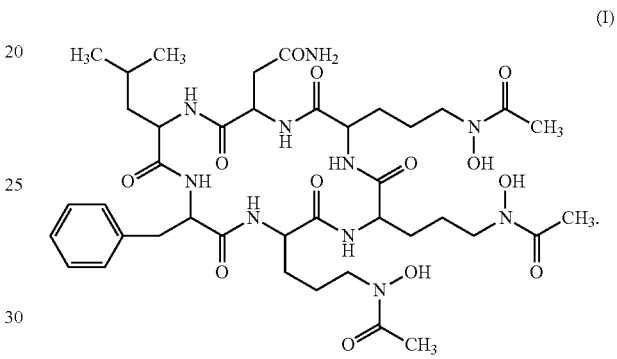

(I)

* * * * *

UNITED STATES PATENT AND TRADEMARK OFFICE
CERTIFICATE OF CORRECTION

PATENT NO. : 8,241,872 B2  
APPLICATION NO. : 12/922675  
DATED : August 14, 2012  
INVENTOR(S) : Ikuko Nakamura et al.

Page 1 of 1

It is certified that error appears in the above-identified patent and that said Letters Patent is hereby corrected as shown below:

On the Title Page

Item (73), "Assignee:   Astellas Pharma Inc., Tokyo (JP)" should read  
--Assignees: Astellas Pharma Inc., Tokyo (JP)  
SIRIM Berhad, Selangor Darul Ehsan (MY)  
TropBio Research Sdn. Bhd., Kuala Lumpur (MY)--.

Signed and Sealed this  
Twenty-first Day of May, 2013

Teresa Stanek Rea  
*Acting Director of the United States Patent and Trademark Office*